United States Patent
Gatta et al.

(10) Patent No.: US 11,776,082 B2
(45) Date of Patent: Oct. 3, 2023

(54) HEALTH AND SAFETY COMPLIANCE SYSTEM, METHODS, AND PRODUCTS

(71) Applicant: DATA DISPLAY SYSTEMS, LLC, Philadelphia, PA (US)

(72) Inventors: Robert F. Gatta, Philadelphia, PA (US); Deborah M. Moulder, Philadelphia, PA (US); Brian J. Pavlichko, Philadelphia, PA (US); Jeffrey S. Porter, Philadelphia, PA (US)

(73) Assignees: Robert F. Gatta, Philadelphia, PA (US); Deborah M. Moulder, Philadelphia, PA (US); Brian J. Pavlichko, Philadelphia, PA (US); Jeffrey S. Porter, Philadelphia, PA (US)

( * ) Notice: Subject to any disclaimer, the term of this patent is extended or adjusted under 35 U.S.C. 154(b) by 575 days.

(21) Appl. No.: 17/083,225

(22) Filed: Oct. 28, 2020

(65) Prior Publication Data
US 2021/0350489 A1    Nov. 11, 2021

Related U.S. Application Data

(60) Provisional application No. 63/020,270, filed on May 5, 2020.

(51) Int. Cl.
*G06Q 50/26* (2012.01)
*G06K 7/10* (2006.01)
(Continued)

(52) U.S. Cl.
CPC .............. *G06Q 50/265* (2013.01); *A61L 2/10* (2013.01); *A61L 2/16* (2013.01); *B05B 12/004* (2013.01); *G01K 3/005* (2013.01); *G01K 13/20* (2021.01); *G01P 13/00* (2013.01); *G06F 3/0481* (2013.01); *G06K 7/1097* (2013.01); *G06K 7/10297* (2013.01); *G06K 7/10415* (2013.01); *G06K 7/10861* (2013.01); *G06T 7/20* (2013.01); *G06T 7/70* (2017.01); *G07C 9/10* (2020.01);
(Continued)

(58) Field of Classification Search
CPC ........ G06Q 50/265; G06T 7/70; G16H 40/67; G16H 40/20; G16H 50/30; G16H 10/20; G07C 9/10; G01K 13/20; G01K 3/005; A61L 2/10; A61L 2/16; B05B 12/004; G01P 13/00; G06F 3/0481; G06K 7/10297
See application file for complete search history.

(56) References Cited

U.S. PATENT DOCUMENTS

| 11,204,281 | B1* | 12/2021 | Ouellette | G08B 21/182 |
| 2022/0078576 | A1* | 3/2022 | Amuduri | G07C 9/27 |
| 2022/0108100 | A1* | 4/2022 | Zhou | H04N 17/002 |

* cited by examiner

*Primary Examiner* — Oleg Korsak
(74) *Attorney, Agent, or Firm* — Heslin Rothenberg Farley & Mesiti P.C.; Victor A. Cardona, Esq.

(57) ABSTRACT

A health and safety compliance system includes processor(s), where the processor(s) are communicatively coupled to a user interface. The user interface includes a display screen, where the display screen is capable of displaying electronic image(s) and is communicatively coupled to the processor(s). The system also includes (i) a sensor unit that is communicatively coupled to the processor(s) and is capable of detecting motion of a user, (ii) a liquid dispensing unit that is communicatively coupled to the processor(s), and (iii) a temperature detection unit that is communicatively coupled to the processor(s).

28 Claims, 6 Drawing Sheets

(51) Int. Cl.
  *G16H 40/20* (2018.01)
  *G16H 50/30* (2018.01)
  *G16H 10/20* (2018.01)
  *G07C 9/10* (2020.01)
  *G01K 3/00* (2006.01)
  *G01P 13/00* (2006.01)
  *A61L 2/16* (2006.01)
  *A61L 2/10* (2006.01)
  *B05B 12/00* (2018.01)
  *G06T 7/70* (2017.01)
  *G06T 7/20* (2017.01)
  *G06F 3/0481* (2022.01)
  *G16H 40/67* (2018.01)
  *G01K 13/20* (2021.01)
  *G06K 19/06* (2006.01)
  *G06K 19/07* (2006.01)

(52) U.S. Cl.
  CPC ............. *G16H 10/20* (2018.01); *G16H 40/20* (2018.01); *G16H 40/67* (2018.01); *G16H 50/30* (2018.01); *A61L 2202/11* (2013.01); *A61L 2202/14* (2013.01); *G06K 19/06028* (2013.01); *G06K 19/06037* (2013.01); *G06K 19/0727* (2013.01); *G06K 19/0728* (2013.01); *G06K 2007/10504* (2013.01); *G06T 2207/30196* (2013.01)

HEALTH AND SAFETY COMPLIANCE SYSTEM, METHODS, AND PRODUCTS

CROSS REFERENCE TO RELATED APPLICATION

This application claims priority to U.S. Provisional Application Ser. No. 63/020,270; filed on May 5, 2020 entitled "Health and Safety Compliance System", the entire disclosure of which is incorporated by reference

TECHNICAL FIELD

One or more aspects broadly relate to a telehealth device and system and more specifically to a health and safety compliance device.

BACKGROUND

Typical telehealth devices and systems are used to provide medical or other health-related information electronically using telecommunication technology. Telehealth technology may include, for example, live video conferencing, which provides real-time interactive communication between a patient or visitor and a physician, other practitioner, or employer across a telecommunications network. Additionally, telehealth technology may include mobile health applications, remote patient monitoring devices, medical kiosks, or other healthcare-related devices.

Telehealth technology provides many benefits for obtaining, analyzing, or processing health-related information remotely. The remote nature of telehealth technology may reduce the need for direct person-to-person interaction. Avoiding person-to-person interaction may be advantageous for performing health-related services while reducing the risk that pathogens may spread from one person to another.

Accordingly, providing telehealth technology enhancements is an area of interest and continued research.

SUMMARY OF THE INVENTION

Shortcomings of the prior art are overcome, and additional advantages are provided, through the provision of a health and safety compliance system that includes one or more processors that are communicatively coupled to a user interface. The user interface includes a display screen, where the display screen is capable of displaying one or more electronic images and the display screen is communicatively coupled to the one or more processors. The system further includes a sensor unit capable of detecting motion of a user, where the sensor unit is communicatively coupled to the one or more processors. Further, a liquid dispensing unit is communicatively coupled to the one or more processors, and a temperature detection unit is communicatively coupled to the one or more processors.

A computer-implemented method is also provided. The method includes providing, by one or more processors and via a user interface of an electronic device, one or more interactive elements, the one or more interactive elements including a request for a user to perform an action. The one or more processors can determine that the action was performed by the user and provide, via the user interface and based on the determining that the first action was performed, at least one other interactive element of the one or more interactive elements, the at least one other interactive element including an additional request for the user to perform one or more additional actions. The one or more processors can determine whether the one or more additional actions were satisfactorily performed by the user and transmit, based on the determining whether the one or more additional actions were satisfactorily performed, an electronic signal to an other electronic device, where the electronic signal facilitates regulating access to a restricted location via a location-access point that is communicatively coupled, via electronic circuitry, with the electronic device.

Additionally, a computer program product is provided that includes a computer readable storage medium readable by a processing circuit and storing instruction for execution by the processing circuit to perform a method. The method includes providing, by one or more processors of the processing circuit and via a user interface of an electronic device, one or more interactive elements, the one or more interactive elements including a request for a user to perform an action. The one or more processors can determine that the action was performed by the user and provide, via the user interface and based on the determining that the action was performed, at least one other interactive element of the one or more interactive elements, the at least one other interactive element including an additional request for the user to perform one or more additional actions. The one or more processors can determine whether the one or more additional actions were satisfactorily performed by the user and transmit, based on the determining whether the one or more additional actions were satisfactorily performed, an electronic signal to an other electronic device, where the electronic signal facilitates regulating access to a restricted location via a location-access point that is communicatively coupled, via electronic circuitry, with the electronic device.

Another computer-implemented method is provided that includes providing, by one or more processors and via a user interface of an electronic device, one or more interactive elements, where the one or more interactive elements include a request for a user to perform an action. The one or more processors determine that the action was performed by the user. Based on determining that the action was performed, at least one other interactive element of the one or more interactive elements is provided, via the user interface, where the at least one other interactive element includes an additional request for the user to perform one or more additional actions. The one or more processors determine that the one or more additional actions were not satisfactorily performed by the user, and based on determining that the one or more additional actions were not satisfactorily performed by the user, the one or more processors send a notification to an other electronic device of an other user.

Additional features and advantages are realized through the concepts described herein.

BRIEF DESCRIPTION OF THE DRAWINGS

One or more aspects are particularly pointed out and distinctly claimed as examples in the claims at the conclusion of the specification. The foregoing and other objects, features, and advantages of one or more aspects are apparent from the following detailed description taken in conjunction with the accompanying drawings in which:

DETAILED DESCRIPTION

Each embodiment presented below facilitates the explanation of certain aspects of the disclosure and should not be interpreted as limiting the scope of the disclosure. Moreover, approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value. When introducing elements of various embodiments, the articles "a," "an," "the," and "said" are intended to mean that there are one or more of the elements. The terms "comprising," "including," and "having" are intended to be inclusive and mean that there may be additional elements other than the listed elements. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. Any examples of operating parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein In accordance with principles of the present invention, systems and methods described herein facilitate processing health-related information. In one example, an environment for health and safety compliance is described that may assist in the capture of health-related data and ensure the health-related data satisfies pre-specified health-related compliance standards in order to access a physical location. In particular, disclosed herein are devices, systems, and methods for providing health and safety compliance by screening users prior to providing access to a physical location.

Figure 1:
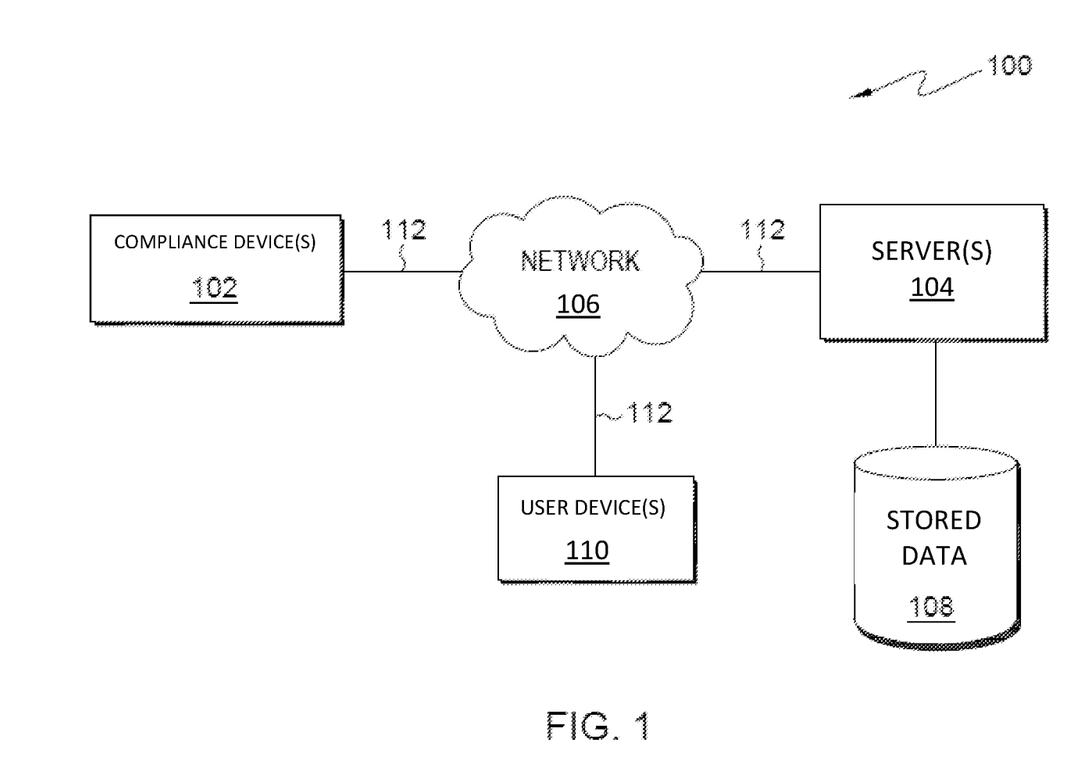
FIG. 1 depicts an example environment to incorporate and use aspects described herein.

FIG. 1 depicts an example environment 100 to incorporate and use aspects described herein. Environment 100 includes health and safety compliance device(s) 102 that communicate with server(s) 104 via network(s) 106. Health and safety compliance device(s) 102 may include any computer system device, examples of which may include mobile devices, tablets, touch-screen devices, display devices, digital kiosks, etc. Further, health and safety compliance device(s) 102 can include one or more processors communicatively coupled to a user interface that includes a display screen where the display screen is capable of displaying one or more electronic images. Further, the display screen can be communicatively coupled to the one or more processors. Health and safety compliance device(s) 102 can also include a sensor unit capable of detecting motion of a user, where the sensor unit is also communicatively coupled to the one or more processors. Additionally, health and safety compliance device(s) 102 can include a liquid dispensing unit and a temperature detection unit that are communicatively coupled to the one or more processors. According to one embodiment, the one or more processors are communicatively coupled to a location-access point, wherein the location-access point facilitates accessing a restricted location.

Server(s) 104 include one or more remote computer systems/servers to perform aspects described herein, such as intelligent processing, generation of digital messages to be presented via a user interface of health and safety compliance device(s) 102, and/or transmission of signals for permitting access to a restricted physical location, e.g. in a work environment. The digital messages may include screening question information and may optionally be stored, along with other user data, such as recorded temperature readings, on a database, file server(s), a public or private cloud storage service platform, etc. represented by stored data 108. According to one embodiment, stored data 108 may be stored at a remote location.

Electronic device(s) 110 may include, for example, a computing device including, without limitation, a mobile device, cellular phone, tablet computer, personal computer, laptop computer, or other computing device that may be configured to receive communication such as, for example, a text message sent by a text messaging service component through a short message service (SMS) or multimedia messaging service (MMS) gateway, and/or email. Electronic device(s) 110 may be in communication with health and safety compliance device(s) 102. In one particular example, electronic device(s) 110 of one or more individuals and/or one or more groups of individuals can receive digital message(s) about inputs received from user(s) of respective health and safety compliance device(s) 102 and/or conditions detected by health and safety compliance device(s) 102.

Network(s) 106 include wireless and/or wireless network(s), such as one or more local area networks and/or one or more wide area networks, such as the internet. Specifically, health and safety compliance device(s) 102 are in communication with network(s) 106 and server(s) 104 via wired or wireless communication links 112, such as wired and/or cellular, Wi-Fi, or other types of wireless communication. More generally, communication links 112 may be any appropriate wireless or wired communication links for communicating data. The communication between health and safety compliance device(s) 102 and server(s) 104 may include sending and receiving of encrypted or otherwise secure data. In a particular example, a recipient of an encrypted message sent from health and safety compliance device(s) 102 is to decrypt the message.

According to one embodiment, the secure data may only be accessed via passwords and/or biometric identification to ensure that only authorized users have access to the secure data for security purposes. Various known techniques can be used to provide security and authentication. For example, environment 100 may include one or more aspects or employ various mechanisms to ensure that unencrypted data is not permanently stored on health and safety compliance device(s) 102. For instance, environment 100 can include a timer, counter, or other flag to invoke deletion of certain portions of the data. According to one embodiment, flash memory may be employed for storing such data so that personally identifying information may be purged when health and safety compliance device(s) 102 is/are turned off. Various other processes may be performed to protect certain user data.

FIG. 1 is just one example of environment 100 to incorporate and use aspects described herein; many other examples are possible and contemplated as being compatible with the capabilities described herein.

Figure 2:
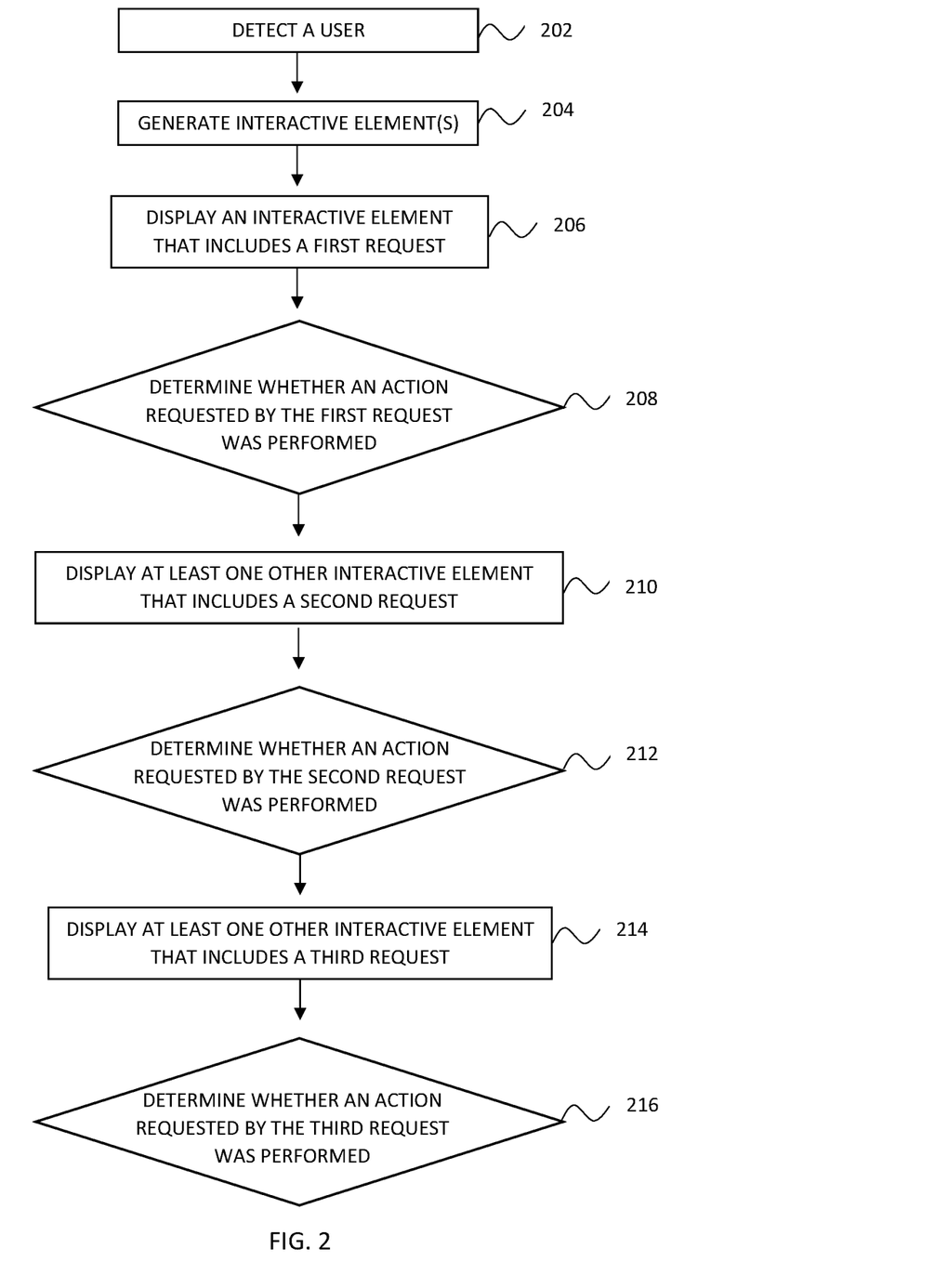
FIG. 2 depicts an example overview of data processing in a telehealth device environment, in accordance with aspects described herein.

Referring to FIG. 2, a conceptual overview of data processing in a telehealth device environment is depicted. Data processing may be performed by use of a computer, such as server(s) 104 and/or health and safety compliance device(s) 102 of environment 100 of FIG. 1. Data processing may process computer usable program code or instructions implementing processes such as disclosed herein.

In the depicted example, at block 202 a user may be detected by health and safety compliance device(s) 102 based on, for example, the user entering an area being monitored by a motion detection unit. Health and safety compliance device(s) 102 may be previously configured to display, via a user interface, one or more interactive elements, e.g., a questionnaire, based on detecting motion from a user. For instance, health and safety compliance device(s) 102 may be programmed to provide a default display of a home screen, a set of images, videos, or other visual content. For instances in which multiple health and safety compliance devices 102 are connected across a network 106, the default display may include a generic display, e.g. 'safety tip of the week,' displayed on each of the multiple health and safety devices 102. Alternatively, the default display may be customizable, e.g. 'open enrollment this Wednesday,' for each health and safety compliance device(s) 102 to display information specific to a physical location. Detecting motion from a user may initiate a display change on the user interface, e.g. cause health and safety compliance device(s) 102 to stop displaying the default display, and generate, at block 204 and via the user interface, the one or more interactive elements for display. The one or more interactive elements may include one or more requests of actions for the user to perform.

In one embodiment, health and safety compliance device(s) 102 may receive a series of digital images to be displayed as, e.g., a looping slide show, on the user interface. The series of digital images may be remotely uploaded, e.g. by one or more remotely connected administrators, in various file formats (i.e., JPEG, PNG, MP4, MP3, etc.). Health and safety compliance device(s) 102 may further receive one or more inputs for displaying the series of images such as, e.g., in a particular order, for a given duration, and/or with animation effects between images. Further, the series of images may be remotely modified and/or customized across a network. The series of images may be viewed, according to one embodiment, remotely to identify an image being displayed on health and safety compliance device(s) 102 at a given moment. For example, health and safety compliance device(s) 102 may include image capture capability for remotely viewing, e.g. taking a snapshot, the user interface so that a remotely connected administrator(s), e.g. connected via electronic device(s) 110, may determine that a correct image/message is being displayed.

Further, according to one embodiment, health and safety compliance device(s) 102 may include a motion sensor to detect motion from a user within a given distance of health and safety compliance device(s) 102. The motion sensor may be triggered, based on detecting movement, which may prompt health and safety compliance device(s) 102 to transition from the default display to an interactive display that includes the interactive elements. According to one embodiment, the interactive elements may include a visual prompt to instruct a user to interact with health and safety compliance device(s) 102.

At block 206, health and safety compliance device(s) 102 may display, via the user interface, an interactive element that includes a first request, the first request instructing the user to perform a first action. For instance, the first action requested by the first request may include, according to one embodiment, a request for the user to position their hands near a bottom portion of health and safety compliance device(s) 102 in order to receive a distribution of sanitizing liquid. Health and safety compliance device(s) 102 may then determine, at block 208, whether the first action requested has been performed. For instance, a motion sensor of health and safety compliance device(s) 102 may detect that the user positioned their hands near the bottom portion of health and safety compliance device(s) 102 in order to receive the distribution of sanitizing liquid. Alternatively, health and safety compliance device(s) 102 may determine that sanitizing liquid was distributed, where the distribution of the sanitizing liquid is motion activated. The determination, at block 208, may be performed based on detecting the first action or, alternatively after a passage of time. For instance, after a predetermined amount of time, e.g. 60 seconds, if the first action has not been detected by health and safety compliance device(s) 102, the time period for performing the first action may time out and the user interface may revert to the default display. Advantageously, requiring the sanitizing liquid to be dispensed may increase the likelihood that the user applies the sanitizing liquid to a device contacting surface, e.g. their hands, gloved hands, finger, etc., so that when the user touches health and safety compliance device(s) 102 their hands will have been recently sanitized. Further, dispensing the sanitizing liquid may increase the likelihood that the user, e.g. an employee, enters a restricted location/area with recently sanitized hands.

In another embodiment, the first action requested may be for the user to provide an input, e.g. via the user interface, in response to an inquiry. According to various embodiments, the user interactions may include various other user interactions.

Additionally, according to one embodiment, a count may be maintained of a number of times the first action has been performed. For instance, health and safety compliance device(s) 102 may maintain the count in memory and/or a remote database may maintain the count, e.g. in stored data 108. Based on the count reaching a predetermined value, a notification may be provided, which indicates that the count has reached the predetermined value. For example, the predetermined value may represent a number of times the sanitizing liquid has been distributed, and the notification, e.g. a text message sent via an SMS or MMS gateway and/or an email notification, may be sent to a remotely connected administrator(s), e.g. connected via electronic device(s) 110, and may include a request for the sanitizing liquid to be refilled. In particular, each instance of the sanitizing liquid being dispensed may be tracked and based thereon the count corresponding to each instance of the liquid being dispensed may be incremented each time the sanitizing liquid is dispensed. Once the sanitizing liquid has been distributed a certain number of times such that the count reaches the predetermined value, the notification may be distributed to a remotely connected electronic device of a remotely connected administrator(s) where the notification indicates that the liquid needs to be replenished. The predetermined value for when to distribute the notification indicating that the liquid needs to be replenished may be a customizable threshold that is set, for example, by an end user. Alternatively, a text and/or email notification may be sent to remotely connected administrator(s) at regular intervals to request for the sanitizing liquid to be refilled. In another example, the predetermined value may represent a number of times the user interface has been touched by a user, and the notification may include a request for the user interface to be cleaned and/or sanitized. In particular, if the first action requested is that the user provide an input via the user interface, each instance of a user providing an input, via the user interface, may be tracked and based thereon the count may correspond to each instance that the user interface is touched or otherwise contacted and/or each time an input is received via the user interface. For example, the count may be incremented each time a touch of the user interface is detected and/or each time an input is received via the user interface. Once the count has reached the predetermined value, the notification may be distributed to a remotely connected electronic device of a remotely connected administrator(s) where the notification indicates that the user interface of health and safety compliance device(s) 102 needs to be cleaned and/or sanitized. As indicated above, the predetermined value for when to distribute the notification that the user interface needs to be cleaned may be a customizable threshold that is set, for example, by an end user.

Based on detecting user compliance of the action requested, health and safety compliance device(s) 102 may display, at block 210 and via the user interface, at least one other interactive element. The other interactive element may include a second request, where the second request instructs the user to perform a second action. If an interactive element of the at least one other interactive element is not completed within a desired timeframe, e.g. 60 seconds, after displaying the interactive element, the user interface of health and safety compliance device(s) 102 may return to the default display until a user is detected.

According to one embodiment, the second action requested by the second request may include a request for an input of identifying information of the user. For instance, the second action requested may include a request for the user to provide identifying information by, for example, scanning a card, swiping a badge, inputting an employee identification number, or other methods used to identify the user. Health and safety compliance device(s) 102 can include, for example, an optical sensor or other optical input device, e.g. a reader, scanner, etc., capable of scanning a unique identifier token provided, via a portable user device (e.g. a mobile phone), by a user. Also, the optical sensor of health and safety compliance device(s) 102 is communicatively coupled to processor(s) of the health and safety compliance system. Health and safety compliance device(s) 102 may include a near-field-communication-enabled device or may include a barcode reader, magnetic stripe card reader, scanner, camera, or other input-receiving device, and may request that the user swipe or scan a unique identifier token such as, e.g., an RFID, barcode, QR code. Additionally, or alternatively, health and safety compliance device(s) 102 may request that a user manually input the identifying information, e.g. pressing a numeric code/pin depending on the access control system of the telehealth device environment. For instances in which a numeric code/pin is provided, the user may need to provide an indication that the numeric code is complete, e.g. click or press a 'submit' or 'enter' button. Optionally, the identifying information may be stored in an on-site database, and/or stored in a remote database as a secure electronic record, e.g. in stored data 108, which may enable the user's identity to be verified by comparing the identifying information with saved user identification information. For instance, the secure electronic record may store encrypted or otherwise confidential identifying information of the users allowing, for example, a remotely connected administrator(s) and/or an automated system to access and/or verify the identifying information in real time and/or at a later time. Optionally, users may be associated with nondescript identification labels and/or numbers stored by a remote database.

According to another embodiment, the second action requested may include a request for the user to respond to a series of questions. Optionally, the series of questions may be a third action requested, fourth action requested, etc., e.g. based on the second action requested being one of the aforementioned embodiments. The actions requested by health and safety compliance device(s) 102 may have various sequences based on desired sequences of operations. The series of questions may, according to one embodiment, include customized preprogrammed questions that may be input by an end user (e.g. a company, business, etc.) and/or questions received from a remotely connected administrator(s), e.g. via electronic device(s) 110, in real-time. For instance, the series of questions may be unique to each end user such that each end user may include different questions as part of the series of questions. Alternatively, the preprogrammed questions may be customized based on location such that one group of health and safety compliance device(s) 102 in one state show a specific set of questions and another group of health and safety compliance device(s) 102 in another state show a separate set of questions. For example, a company with offices in different states, e.g. New York and Pennsylvania, may designate that all health and safety compliance device(s) 102 in one state, e.g. New York, include a specific set of questions that is different than the separate set of questions used in the other state, e.g. Pennsylvania. The specific set of questions may be specific to that one state, e.g. New York, and would not be applicable to the other state, e.g. Pennsylvania, where the company has an office. Additionally, preprogrammed answers corresponding to the customized preprogrammed questions may be stored, e.g. in stored data 108, and compared to answers provided by the users. For instance, if answer(s) received from the user in response to one or more of the series of questions is unacceptable, e.g. based on comparing the answer to a preprogrammed acceptable answer, this may automatically trigger a message, notification, or other signal to be sent to electronic device(s) 110 of a remotely connected administrator(s) or otherwise communicated to a remotely connected administrator(s) and/or one or more on-site individuals. Advantageously, once the message, notification, or other signal is sent, the remotely connected administrator(s) and/or one or more on-site individuals may be able to communicate with the user, e.g. via health and safety compliance device(s) 102 or via a mobile device of the user, to ask additional questions in real-time. Further, the remotely connected administrator(s) and/or one or more on-site individuals may be able to determine, based on the user's answers, whether to permit the user to enter a restricted location/area.

According to one embodiment, the series of questions may include yes/no questions with predefined touch areas corresponding to yes and no, respectively. According to one embodiment, the series of questions may be worded such that each question requires the same answer, e.g. the acceptable answer to each question is a 'no' answer. For example, the questions may ask the user if the user has been outside of an approved safe zone within the past 14 days, ask if the user has recently exhibited any symptoms of a sickness, e.g. a cough, runny nose, high temperature, etc., or if the user has recently come into contact with a person who is sick. If one or more of the answers provided by the user are not considered an acceptable answer, based on the acceptable answers being preprogrammed and/or otherwise indicated in real-time by a remotely connected administrator(s), then the user interface of health and safety compliance device(s) 102 may provide a verification indication for the user to verify that the information provided by the one or more answers not considered to be an acceptable answer is accurate. Optionally, if a response to a question of the series of questions is not received within a desired timeframe, e.g. 60 seconds, after displaying the question, the user interface of health and safety compliance device(s) 102 may return to the default display until a user is detected. The series of questions may be customizable by, for example, remote administrator(s) and may include translations into other languages and/or be programmed to ask the series of questions in various language formats.

According to one embodiment, the request for the user to respond to the series of questions may be a third action if, for instance, the second action included a request for identifying information and the user provided an indication that they are a visitor (i.e., does not have an employee identification number). Further, the request for the user to respond to the series of questions may be a third action if, for instance, the second action included a request for identifying information and the series of questions are associated with the identifying information. For example, users may be given a particular series of questions that is linked to the user's identifying information, e.g. customized questions specific to an account for that user. According to one embodiment, if the series of questions is linked to the user's identifying information, the series of questions may be previously accessed and answered by the user and the user may scan in, e.g. via a QR code, the answers (i.e. a filled-out questionnaire). For instance, the series of questions may be associated with a QR code or another form of near field communication that the user may scan or otherwise transmit from a mobile device or other personal device. For example, a user, e.g. an employee, may be provided with the series of questions via, e.g., a mobile application, text message, and/or email accessible on a mobile device of the user that may enable the user to answer the series of questions without having to provide inputs directly into health and safety compliance device(s) 102. Further, answers to the series of questions may be transmitted, by the user and via the user's mobile device, via near field communication to health and safety compliance device(s) 102. Optionally, answers provided by the user to the series of questions may be stored in an on-site database, and/or stored in a remote database, e.g. as stored data 108, where, for example, the answers are linked to the user's identifying information and may be remotely accessed by the remotely connected administrator(s).

According to another embodiment, the second action requested by the second request may include a request for the user to provide a real-time temperature reading. Optionally, the real-time temperature reading may be a third action requested, fourth action requested, etc., e.g. based on the second action requested being one of the aforementioned embodiments. The actions requested by health and safety compliance device(s) 102 may have various sequences based on desired sequences of operations. The real-time temperature reading may be administered, e.g., using a forehead thermometer, via health and safety compliance device(s) 102. According to one embodiment, the temperature reading may be obtained via a contactless temperature reader where the user does not need to contact the temperature reader in order for their temperature to be taken. For instance, the request may indicate that the user is to position their forehead within a predetermined distance, e.g. 0-15 inches or more specifically 10 inches, of a temperature sensor of health and safety compliance device(s) 102. For example, health and safety compliance device(s) 102 can include a camera to facilitate aligning a location of the user, e.g. the user's forehead, with a temperature sensor of the temperature detection unit. Based thereon, the user interface may display an image of a user, captured via the camera, positioning their head near a temperature sensor of health and safety compliance device(s) 102. According to one embodiment, the temperature sensor may be controlled by, e.g., a microcontroller unit located next to or otherwise incorporated with an internal camera positioned on a top portion of health and safety compliance device(s) 102. Based upon the real-time temperature reading being administered, temperature data of the real-time temperature reading may be processed and compared to a predefined acceptable temperature range, where the user's real-time temperature must fall within the acceptable range in order for the user to be granted access, via a location-access point, to the restricted location. The predefined acceptable temperature range may be set, customized and/or changed by, for example, a remotely connected administrator(s). For instance, the acceptable temperature range may be, e.g., between 97° and 99.5° Fahrenheit.

According to one embodiment, the commands for processing temperature data are transmitted across network 106 between health and safety compliance device(s) 102 and server 104.

Based on processing the temperature data, health and safety compliance device(s) 102 may display, via a user interface, an indication of whether the real-time temperature reading is within the acceptable temperature range. In one embodiment, if a first real-time temperature reading is within the acceptable temperature range then no further temperature readings are requested; however, if the first real-time temperature reading is not within the acceptable temperature range, then a second temperature reading may be requested. Based on one or more real-time temperature readings being outside of the acceptable temperature range, a notification, e.g. a text or email, may be sent to electronic device(s) 110 of an on-site individual (e.g., an employee, administrator, etc.) so that the on-site individual may verify the real-time temperature reading with another thermometer to determine whether the first real-time temperature reading was accurate and/or to establish a verifiable temperature of the user. According to one embodiment, the temperature detection unit of health and safety compliance device(s) 102 may include a first temperature detection unit, and the system may further include, according to one embodiment, a second temperature detection unit used to verify the real-time temperature reading obtained via the first temperature detection unit. Further, an indication may be provided, via the user interface, if the temperature reading generated an error, e.g. due to improper placement of the user's forehead, where the indication requests that the user repeat the real-time temperature reading.

Health and safety compliance device(s) 102 may also request, as a backup option, that the user push a button or otherwise indicate that the user is ready for the real-time temperature reading. For instance, the user interface may include a 'take measurement' button for the user to touch in order for the temperature sensor to administer the real-time temperature reading. Alternatively, the real-time temperature reading may include a timing element where the user interface displays a countdown to an instance for when the real-time temperature will be read, The user interface may also provide confirmation of a successful real-time temperature reading and/or display the real-time temperature read during the real-time temperature reading.

Optionally, the real-time temperature reading may be stored in an on-site database, and/or stored in a remote database as a log or other record of the users. For embodiments in which health and safety compliance device(s) 102 are being used in a workplace environment, a remotely connected administrator(s), e.g. human resources or environmental health and safety manager, may access the temperature reading data to identify users who may pose a safety risk to others due to, e.g., having a real-time temperature reading outside of the acceptable temperature range.

At block 212, health and safety compliance device(s) 102 determine whether an action requested by a second request was performed. For example, determining whether the action requested by the second request was performed may include determining whether a. temperature reading was provided. According to one embodiment, the indication provided at block 212 may include a request for the user to repeat the second action in order to verify that inputs provided by the user during the second action were correct. For instance, a second real-time temperature reading may be required based on the first real-time temperature reading not being within the acceptable temperature range. According to one embodiment, the indication provided at block 212 may include an instruction, e.g. a 'go' or 'enter' command, to enter a physical location. Other embodiments may include a change in color of a display screen.

At block 214, the user interface may request that the user perform a third action. For instance, according to various embodiments, if the first action was to receive sanitizing liquid and the second action was to input identification information, the third action may include answering the series of questions have been completed or providing the real-time temperature reading requested. According to one embodiment, one or more indications may be provided, via the user interface, once a user completes one or more actions. The indication may be remotely modified, e.g. in real-time, periodically, intermittently, etc. by, e.g., a remotely connected administrator(s). According to one embodiment, the indication may include an auditory signal, e.g. a beep, or other auditory command, or may include a visual indication/message that the other interactive element has been completed.

At block 216, health and safety compliance device(s) 102 determine that the third action requested was performed by the user. According to various embodiments, additional actions beyond three actions may be requested, via the user interface. For instance, if the third action requested was providing the real-time temperature reading, a fourth action requested may include answering the series of questions. The series of question may, for example, be dynamic such that the order of questions and/or questions being asked change may change in response to answers received and/or the real-time temperature reading.

Upon completing the determinations of blocks 212 and/or 216 and compliance with any other actions beyond three actions required by health and safety compliance device(s) 102, a signal may be transmitted to a location-access point of a restricted location to permit access to the restricted location. For instance, based on determining that a second action was satisfactorily completed and based on the second action being the final action of the one or more interactive elements to be completed by the user, an electronic relay may be triggered to complete a circuit to the location-access point (e.g. a door) for a period of time, e.g. 60 seconds, to allow access to the restricted location. According to one embodiment, access to the restricted location can be remotely controlled, via the location-access point, by health and safety compliance device(s) 102. According to one embodiment, the location-access point can include a hinged barrier, slidable barrier, revolving barrier, door, gate, turnstile, or other location access point. According to one embodiment, the signal transmitted may include an electronic relay to complete a circuit with a card reader or solenoid to allow the user to swipe an access badge on a badge reader to unlock the location-access point (e.g. door). According to one embodiment, the location-access point can include a lock that can be unlocked based on a signal being transmitted by health and safety compliance device(s) 102, and/or the location-access point can control an electronic motor used to open, e.g., a door of the location-access point, etc. Various other access methods may be used to provide access to a restricted location via the location-access point. According to other embodiments, the signal may be transmitted after determining the third action, fourth action, etc. is performed rather than after determining that the second action was performed.

According to various embodiments, health and safety compliance device(s) 102 may display a message indicating to the user that one or more actions were not satisfactorily performed. For instance, health and safety compliance device(s) 102 may indicate that one or more answers input by the user in response to the series of questions fails the requirements that the user must satisfy in order for access to be granted to the restricted location. Health and safety compliance device(s) 102 may also provide additional indications such as, for example, an indication that the user is to wait for assistance and that an administrator will contact them and/or will arrive shortly. Additionally, or alternatively, if one or more actions were not satisfactorily performed, remotely connected administrator(s) may be automatically notified by health and safety compliance device(s) 102. Further, if the remotely connected administrator(s) are notified, health and safety compliance device(s) 102 may generate a message indicating to the remotely connected administrator(s) what requirement was not satisfactorily performed by the user. Optionally, health and safety compliance device(s) 102 may provide instructions to the remotely connected administrator(s) for how to resolve the situation. For instance, health and safety compliance device(s) 102 may indicate that the remotely connected administrator(s) should notify the user that one or more actions were not satisfactorily performed, and that the user may not enter the restricted location. Health and safety compliance device(s) 102 may also indicate that the administrator or other personnel should assist the user by, for example, taking a secondary temperature check. Additionally, or alternatively, health and safety compliance device(s) 102 may indicate that the remotely connected administrator(s) should notify certain personnel such as, for example, local health officials, company management, security, emergency response personnel, etc. of the situation.

After the period of time is completed, the user interface of health and safety compliance device(s) 102 may return to the default display until another user is detected. According to one embodiment, upon return to the default display, an ultraviolet (UV) light of health and safety compliance device(s) 102 may be activated to disinfect surface(s) of health and safety compliance device(s) 102 that may have been touched by the user. According to one embodiment, health and safety compliance device(s) 102 may include a UV generation unit that includes, for example, an ultraviolet light assembly, an ultraviolet-light emission control unit, a timer used to control how long surface(s) of health and safety compliance device(s) 102 are exposed to UV light, and/or a UV light. For instance, health and safety compliance device(s) 102 may include a UV light assembly configured to sanitize at least one surface of the user interface. In one example, the UV light assembly may be controlled by an ultraviolet-light-emission control unit or a UV generator coupled to the UV light assembly as well as one or more processors. In particular, the UV light assembly may be used to sterilize surface(s) of health and safety compliance device(s) 102 by exposing the surface(s) to UV light for a predetermined amount of time, where the predetermined amount of time is based on, e.g., a surface disinfection rate of the UV light. The UV light-emission control unit or UV generator may be activated, according to one embodiment, upon return to the default display or, alternatively, based on timing, e.g. 60 seconds after an input is received. According to one embodiment, the UV generator may be activated based on programming provided by a remotely connected administrator(s), e.g. remotely activated in real-time, scheduled at regular intervals, etc.

According to various embodiments, a remotely connected administrator(s), e.g. off-site and/or on-site, may change, and or otherwise control content being displayed on the user interface of health and safety compliance device(s) 102.

Figure 3:
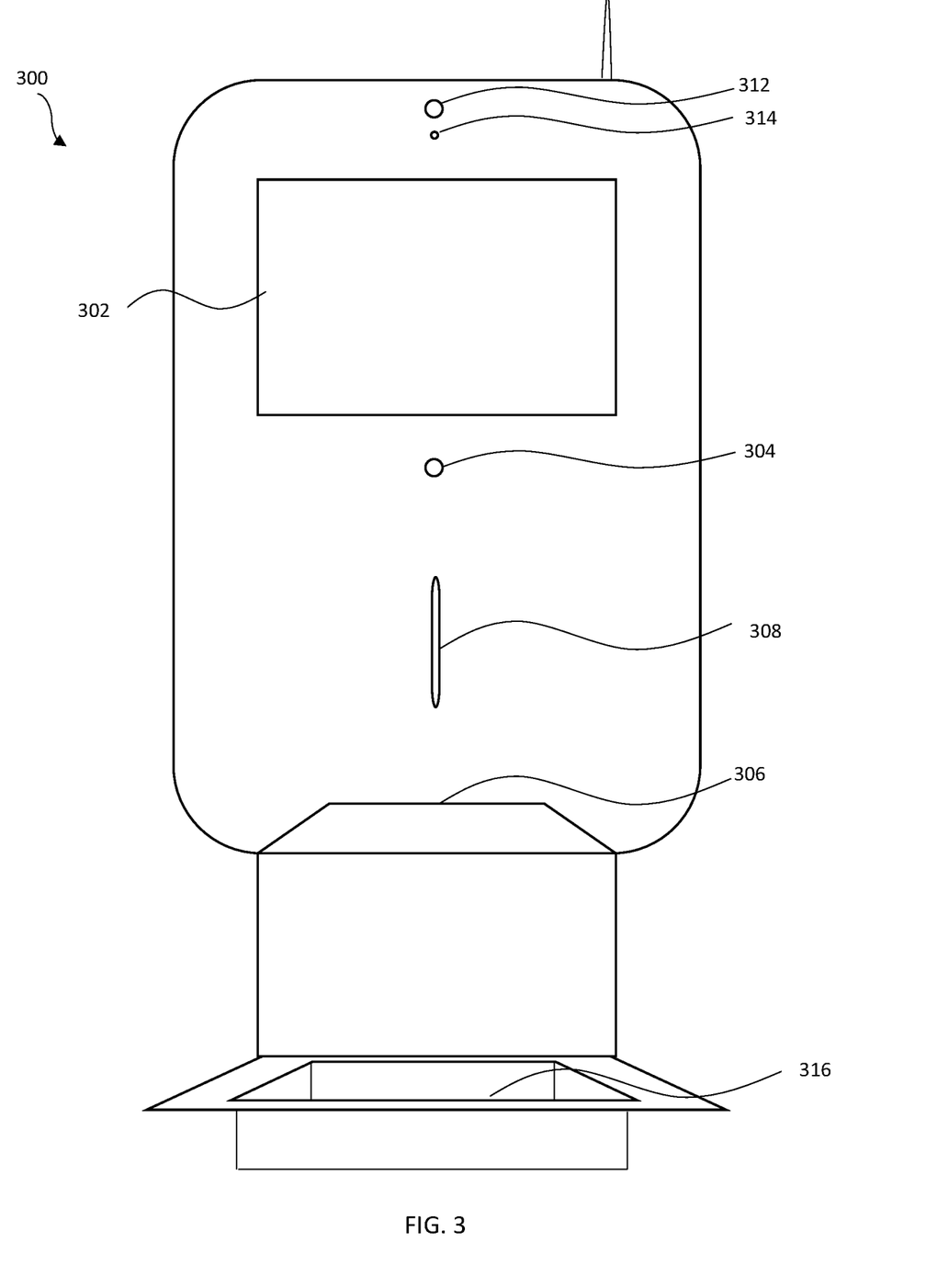
FIG. 3 depicts an example health and safety compliance device, in accordance with aspects described herein.

FIG. 3 depicts an example health and safety compliance device 300. Health and safety compliance device 300 may include a user interface 302, e.g. an interactive screen such as an LCD 10.1" HD touchscreen or 15.6" HD touchscreen, as well as one or more motion sensors 304 for detecting a user and/or positioning of a user's hands, forehead, etc. Health and safety compliance device 300 may also include a sanitizing liquid dispenser 306 for dispensing sanitizing liquid 308 from a storage container. Additionally, an additional motion sensor (not shown) may be located near sanitizing liquid dispenser 306 to detect that a user's hands are positioned below sanitizing liquid dispenser 306. Further, health and safety compliance device 300 may include a mounting for attaching health and safety compliance device 300 to a surface, e.g. a wall. Health and safety compliance device 300 may also include a temperature sensor 312 for obtaining a user's temperature and a camera 314 to, e.g., assist in aligning a user's forehead as described above. Further, health and safety compliance device 300 may include a drip tray 316 for receiving excess sanitizing liquid 308. Health and safety compliance device 300 can be mounted, e.g. to a wall or other surface. According to one embodiment, health and safety compliance device 300 may be mounted to an adjustable column so that a height of health and safety compliance device 300 may be manually and/or automatically adjusted (e.g. via a remote administrator, via the user, etc.).

Figure 4:
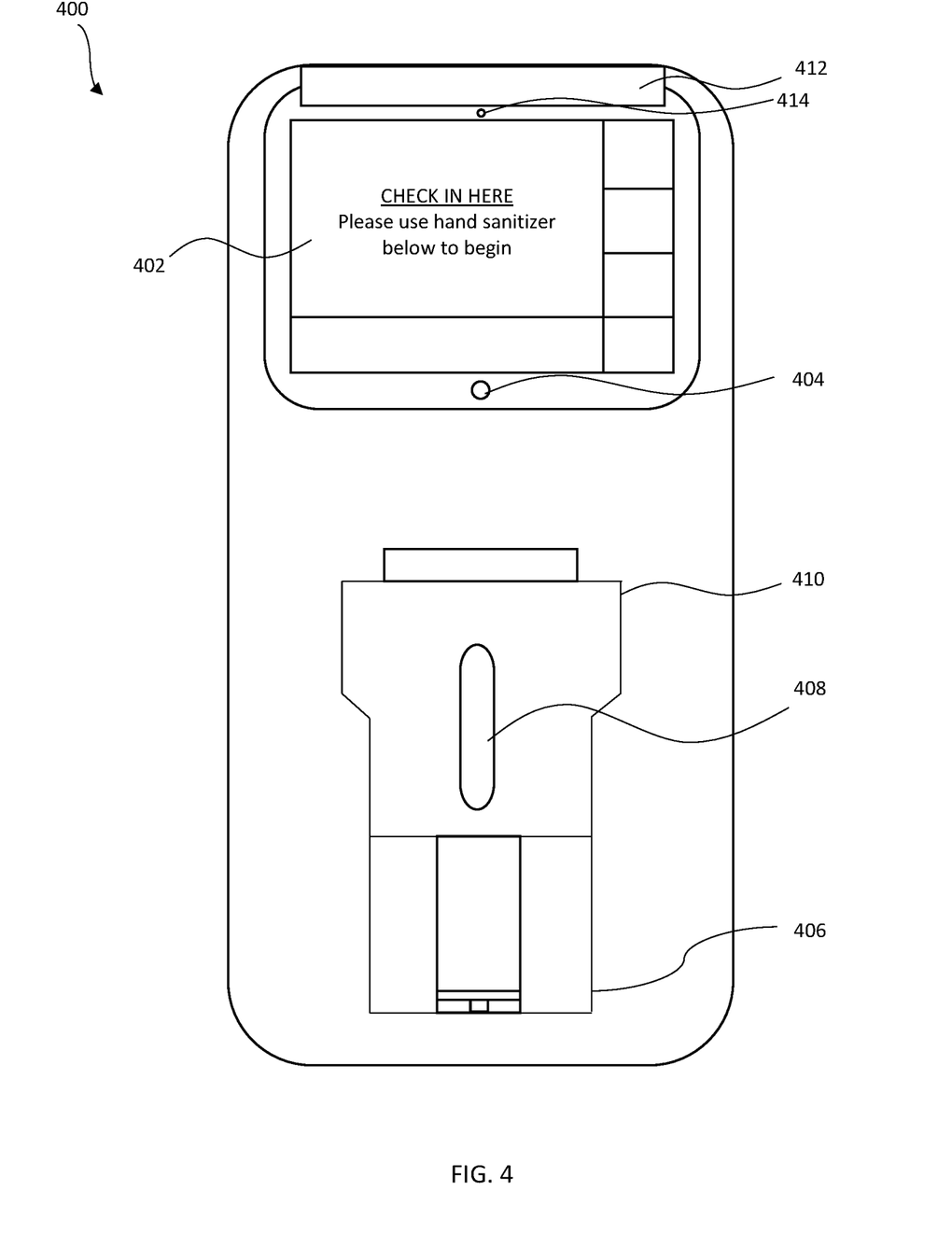
FIG. 4 depicts an example health and safety compliance device, in accordance with aspects described herein.

FIG. 4 depicts an example health and safety compliance device 400. Health and safety compliance device 400 may include a user interface 402, e.g. an interactive screen such as an LCD 10.1" HD touch screen or 15.6" HD touchscreen, as well as one or more motion sensors 404 for detecting a user and/or positioning of a user's hands, forehead, etc. and/or an internal camera 414 to, e.g., assist in aligning a user's forehead as described above. Health and safety compliance device 400 may also include a hands-free, motion-activated sanitizing liquid dispenser 406 for dispensing sanitizing liquid 408 from a storage container 410 onto a device contacting surface (e.g., a user's hands, a stylist, disposable gloves, etc.) to be used, by the user, to touch health and safety compliance device 400. Health and safety compliance device 400 may also include a temperature sensor for obtaining a user's temperature and/or an ultraviolet C (UVC) light 412 operated by a UV generator of health and safety compliance device 400 for emitting UV light to allow a disinfection of device 400 as described above.

Figure 5:
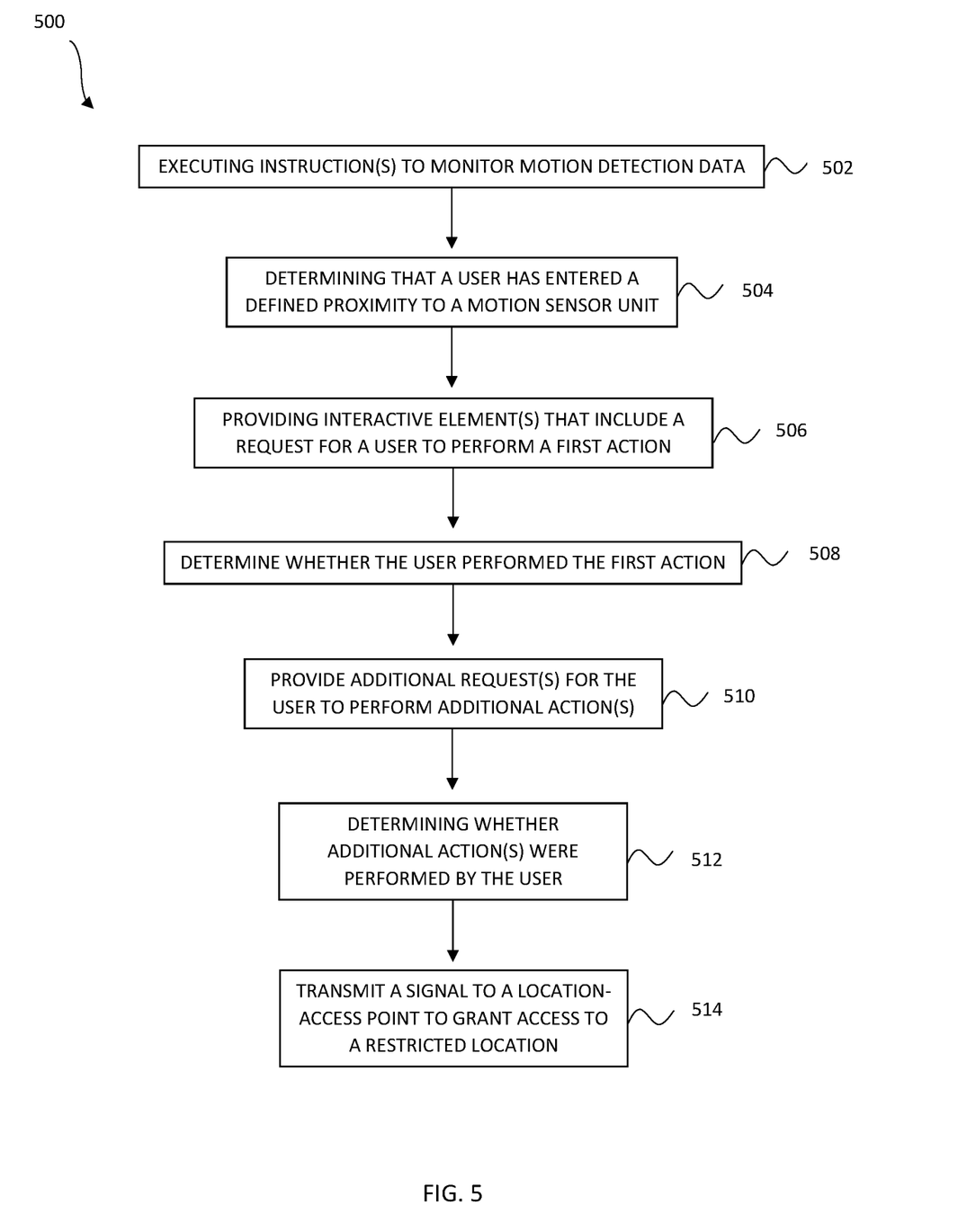
FIG. 5 depicts an example process for health-related data processing in a health and safety compliance environment, in accordance with aspects described herein.

FIG. 5 depicts an example process 500 for health-related data processing in a health and safety compliance environment. Process 500 includes executing, by one or more processors, one or more instructions to monitor 502 motion detection data detected via one or more sensors of a sensor unit of the health and safety compliance device, the motion detection data indicating whether a user has moved within a defined proximity of the sensor unit. Based on processing the motion detection data, determining 504 that a user has entered the defined proximity to the sensor unit, and based on determining the user has entered the motion detection area, providing 506, by the one or more processors and via a user interface of the health and safety compliance device, at least one interactive element, the at least one interactive element including a first request for a user to perform a first action. Further, the process includes determining 508, by the one or more processors, that the first action was performed by the user, and based on determining that the first action was performed, providing 510, by the one or more processors and via the user interface, one or more additional requests for the user to perform one or more additional actions. Based on determining 512, by the one or more processors, that at least one action of the one or more additional actions was performed by the user, the one or more processors may transmit 514, via electronic circuitry, an electronic signal to an access point that is in electronic communication with the health and safety compliance device. The signal facilitates granting access, via the access point, to a restricted location, where the restricted location includes a physical location for the user to enter. In particular, based on receiving the signal, one or more electronic elements may provide access, via the access point, to the restricted location. In other examples, additional actions (e.g., third, fourth or more) may be required prior to allowing access to the restricted location. Such actions could include requiring additional information to be input by a user, e.g. via a touchscreen (e.g., user interface 302, user interface 402), a user's personal device (e.g. mobile device) using near field communication, or other input device, or sensing such information via sensors (e.g., temperature sensor 312, temperature sensor 352) of a safety compliance device (e.g., device 300, device 350, device 400).

According to various embodiments, health and safety compliance device(s) 102 may include any computer system device, examples of which may include health and safety compliance devices 300, 350 and 400, that have one or more sensors for interacting with a user, e.g. by taking the user's temperature, providing a questionnaire, etc. According to various embodiments, although the interactive elements associated with health and safety compliance device(s) 102, 300, 350, 400 can include hand sanitation, identifying information of a user, a questionnaire, a temperature sensor, etc. described above, health and safety compliances device(s) 102, 300, 350, 400 may also include any other health-related inputs as the interactive elements. Additionally, any health-related inputs provided as the interactive elements may be transmitted, for example, to a remote database for access by a remotely connected administrator(s).

Although various examples are provided, variations are possible without departing from a spirit of the claimed aspects.

The computer of the health and safety compliance system may take actions such as providing requests for the user to perform certain actions. In response to determining, by the computer, that the actions have been performed by the user, the computer may transmit an electronic signal to an access point, wherein the signal facilitates granting access to a restricted location via the access point. Advantageously, this ensures that persons who do not satisfy specific criteria do not have access to the restricted location.

Figure 6:
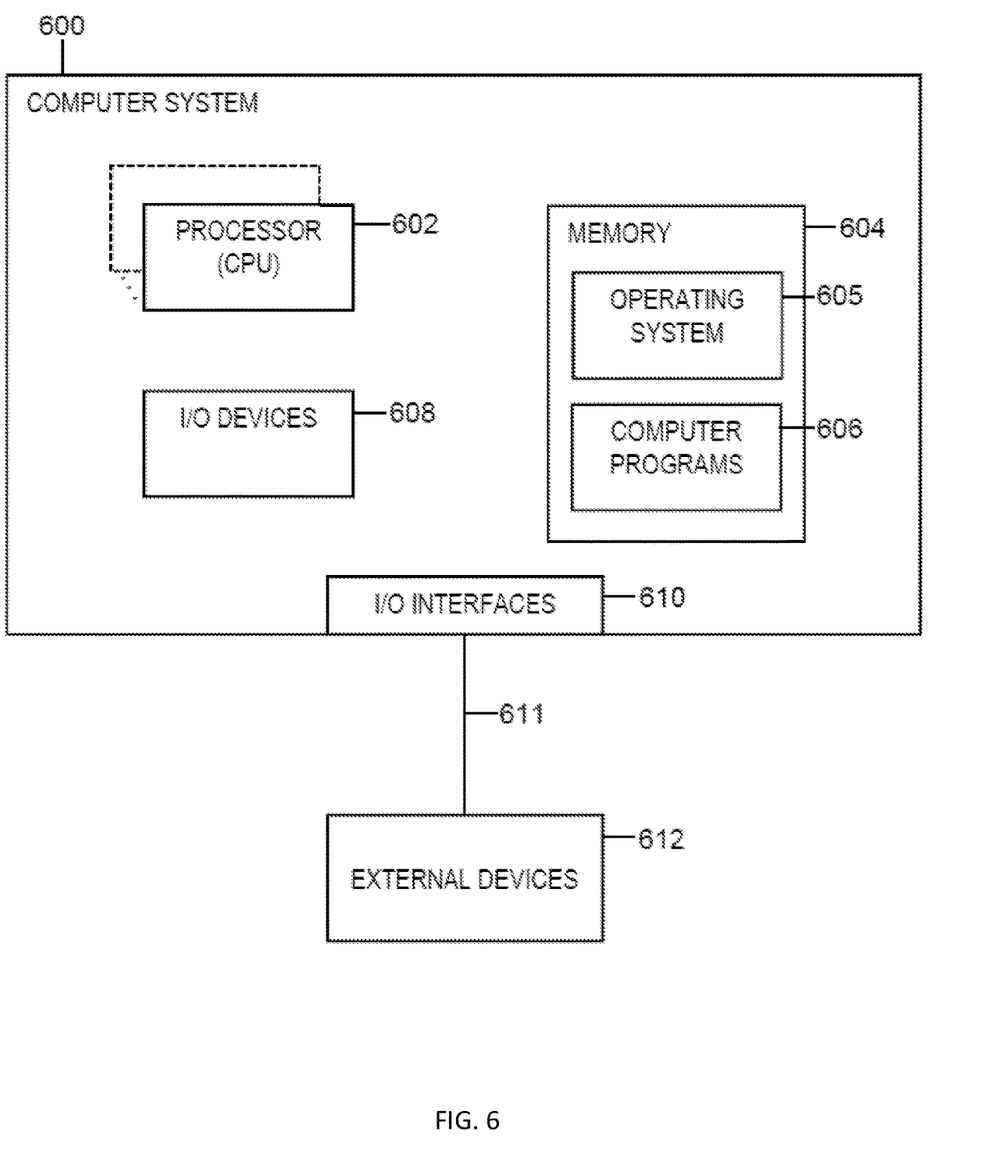
FIG. 6 depicts one example of a computer system and associated devices to incorporate and/or use aspects described herein.

Processes described herein may be performed singly or collectively by one or more computing aspects of the health and safety compliance system. The computing aspects may include one or more messaging servers, databases, client computing devices, or a combination of the foregoing, as examples. FIG. 6 depicts one example of such as computing aspect or computer system and associated devices that can incorporate and/or use aspects described herein. A computer system may also be referred to herein as a data processing device/system, computing device/system/node, or simply a computer. The computer system may be based on one or more of various system architectures and/or instruction set architectures.

FIG. 6 shows a computer system 600 in communication with external device(s) 612. Computer system 600 includes one or more processor(s) 602, for instance central processing unit(s) (CPUs). A processor can include functional components used in the execution of instructions, such as functional components to fetch program instructions from locations such as cache or main memory, decode program instructions, and execute program instructions, access memory for instruction execution, and write results of the executed instructions. A processor 602 can also include register(s) to be used by one or more of the functional components. Computer system 600 also includes memory 604, input/output (I/O) devices 608, and I/O interface 610, which may be coupled to processor(s) 602 and each other via one or more buses and/or other connections. Bus connections represent one or more of any of several types of bus structures, including a memory bus or memory controller, a peripheral bus, an accelerated graphics port, and a processor or local bus using any of a variety of bus architectures.

Memory 604 can be or include main or system memory (e.g. Random Access Memory) used in the execution of program instructions, storage device(s) such as hard drive(s), hard disk drives (HDDs), solid state drives (SSDs), phase-change memory (PCM), flash memory such as NOR flash and NAND flash, or optical media as examples, and/or cache memory, as examples. Memory 604 can include, for instance, a cache, such as a shared cache, which may be coupled to local caches (examples include L1 cache, L2 cache, etc.) of processor(s) 602. Additionally, memory 604 may be or include at least one computer program product having a set (e.g., at least one) of program modules, instructions, code or the like that is/are configured to carry out functions of embodiments described herein when executed by one or more processors.

Memory 604 can store an operating system 605 and other computer programs 606, such as one or more computer programs/applications that execute to perform aspects described herein. Examples of operating system 605 include z/OS, Windows, Linus, UNIX, BSD, SunOS, Solaris, MacOS, or other compatible operating systems including proprietary operating systems. Specifically, programs/applications can include computer readable program instructions that may be configured to carry out functions of embodiments of aspects described herein.

Examples of I/O devices 608 include but are not limited to microphones, speakers, Global Positioning System (GPS) devices, cameras, lights, accelerometers, gyroscopes, magnetometers, sensor devices configured to sense light, proximity, heart rate, body and/or ambient temperature, blood pressure, and/or skin resistance, and activity monitors. An I/O device may be incorporated into the computer system as shown, though in some embodiments an I/O device may be regarded as an external device (612) coupled to the computer system through one or more I/O interfaces 610.

Computer system 600 may communicate with one or more external devices 612 via one or more I/O interfaces 610. Example external devices include a keyboard, a pointing device such as a mouse or a touch pad, a display, and/or any other devices that enable a user to interact with computer system 600. Other example external devices include any device that enables computer system 600 to communicate with one or more other computing systems or peripheral devices such as a printer. A network interface/adapter is an example I/O interface that enables computer system 600 to communicate with one or more networks, such as a local area network (LAN), a general wide area network (WAN), and/or a public network (e.g., the Internet), providing communication with other computing devices or systems, storage devices, or the like. Ethernet-based (such as Wi-Fi) interfaces and Bluetooth® adapters are just examples of the currently available types of network adapters used in computer systems (BLUETOOTH is a registered trademark of Bluetooth SIG, Inc., Kirkland, Washington, U.S.A.).

The communication between I/O interfaces 610 and external devices 612 can occur across wired and/or wireless communications link(s) 611, such as Ethernet-based wired or wireless connections. Example wireless connections include cellular, Wi-Fi, Bluetooth®, proximity-based, near-field, or other types of wireless connections. More generally, communications link(s) 611 may be any appropriate wireless and/or wired communication link(s) for communicating data.

Particular external device(s) 612 may include one or more data storage devices, which may store one or more programs, one or more computer readable program instructions, and/or data, etc. Computer system 600 may include and/or be coupled to and in communication with (e.g. as an external device of the computer system) removable/non-removable, volatile/non-volatile computer system storage media. For example, it may include and/or be coupled to a non-removable, non-volatile magnetic media (typically called a "hard drive"), a magnetic disk drive for reading from and writing to a removable, non-volatile magnetic disk, and/or an optical disk drive for reading from or writing to a removable, non-volatile optical disk, such as a CD-ROM, DVD-ROM or other optical media.

Computer system 600 may be operational with numerous other general purpose or special purpose computer system environments or configurations. Computer system 600 may take any of various forms, well-known examples of which include, but are not limited to, personal computer (PC) system(s), server computer system(s), such as messaging server(s), thin client(s), thick client(s), workstation(s), laptop(s), handheld device(s), mobile device(s)/computer(s) such as smartphone(s), tablet(s), and wearable device(s), multiprocessor system(s), microprocessor-based system(s), telephony device(s), network appliance(s) (such as edge appliance(s)), virtualization device(s), storage controller(s), set top box(es), programmable consumer electronic(s), network PC(s), minicomputer system(s), mainframe computer system(s), cluster computer system(s), and distributed cloud computing environment(s) that include any of the above systems or devices, and the like.

Various implementations of aspects described herein may be performed, for example, via a cloud computing environment. For instance, the cloud computing environment can be implemented in a variety of different ways to best suit different requirements including, for example, public cloud, private cloud, community cloud, hybrid cloud, or combinations thereof. The cloud computing environment may enable some processes previously performed by an organization's information technology department to be performed as service layers within a cloud environment according to the cloud's public/private nature. In accordance with an embodiment, the cloud computing environment may include a combination of one or more Infrastructure as a Service (IaaS) layer, Platform as a Service (PaaS) layer, and/or Software as a Service (SaaS) layer, each of which are delivered as service layers within the cloud environment, and which can be used by consumers within or external to an organization, depending on the particular cloud computing model being used. An embodiment of the cloud computing environment can include computer system 600.

In some embodiments, aspects of the present invention may take the form of a computer program product, which may be embodied as computer readable medium(s). A computer readable medium may be a tangible storage device/medium having computer readable program code/instructions stored thereon. Example computer readable medium(s) include, but are not limited to, electronic, magnetic, optical, or semiconductor storage devices or systems, or any combination of the foregoing. Example embodiments of a computer readable medium include a hard drive or other mass-storage device, an electrical connection having wires, random access memory (RAM), read-only memory (ROM), erasable-programmable read-only memory such as EPROM or flash memory, an optical fiber, a portable computer disk/diskette, such as a compact disc read-only memory (CD-ROM) or Digital Versatile Disc (DVD), an optical storage device, a magnetic storage device, or any combination of the foregoing. The computer readable medium may be readable by a processor, processing unit, or the like, to obtain data (e.g. instructions) from the medium for execution. In a particular example, a computer program product is or includes one or more computer readable media that includes/stores computer readable program code to provide and facilitate one or more aspects described herein.

As noted, program instruction contained or stored in/on a computer readable medium can be obtained and executed by any of various suitable components such as a processor of a computer system to cause the computer system to behave and function in a particular manner. Such program instructions for carrying out operations to perform, achieve, or facilitate aspects described herein may be written in, or compiled from code written in, any desired programming language. In some embodiments, such programming language includes object-oriented and/or procedural programming languages such as C, C++, C#, Java, Python, JavaScript, Go, R, Swift, PHP, Dart, Kotlin, etc.

Program code can include one or more program instructions obtained for execution by one or more processors. Computer program instructions may be provided to one or more processors of, e.g., one or more computer systems, to produce a machine, such that the program instructions, when executed by the one or more processors, perform, achieve, or facilitate aspects of the present invention, such as actions or functions described in flowcharts and/or block diagrams described herein. Thus, each block, or combinations of blocks, of the flowchart illustrations and/or block diagrams depicted and described herein can be implemented, in some embodiments, by computer program instructions.

Although various embodiments are described above, these are only examples. For example, computing environments of other architectures can be used to incorporate and use one or more embodiments.

What is claimed is:

1. A health and safety compliance system comprising:
one or more processors, wherein the one or more processors are communicatively coupled to a user interface;
the user interface comprising a display screen, wherein the display screen is capable of displaying one or more electronic images and wherein the display screen is communicatively coupled to the one or more processors;
a sensor unit capable of detecting motion of a user, wherein the sensor unit is communicatively coupled to the one or more processors;
a liquid dispensing unit communicatively coupled to the one or more processors;
a temperature detection unit communicatively coupled to the one or more processors;
an ultraviolet light assembly configured to sanitize at least one surface of the user interface; and
an ultraviolet-light-emission control unit coupled to the ultraviolet light assembly and the one or more processors, wherein the ultraviolet-light-emission control unit is capable of controlling the ultraviolet light assembly.

2. The health and safety compliance system of claim 1, wherein the one or more processors are communicatively coupled to a location-access point, wherein the location-access point facilitates accessing a restricted location.

3. The health and safety compliance system of claim 2, wherein the location-access point comprises a hinged barrier, a slidable barrier, or a revolving barrier.

4. The health and safety compliance system of claim 1, further comprising a camera, the camera facilitating aligning a location of the user with a temperature sensor of the temperature detection unit.

5. The health and safety compliance system of claim 1, wherein the temperature detection unit is a first temperature detection unit, and wherein the system further comprises a second temperature detection unit.

6. The health and safety compliance system of claim 1, further comprising an optical sensor capable of scanning a unique identifier token provided, via a portable user device, by the user, wherein the optical sensor is communicatively coupled to the one or more processors.

7. The health and safety compliance system of claim 6, wherein the unique identifier token provided by the user comprises an RFID, a barcode, a magnetic card, or a QR code.

8. A computer-implemented method comprising:
providing, by one or more processors and via a user interface of an electronic device, one or more interactive elements, the one or more interactive elements including a request for a user to perform an action;
determining, by the one or more processors, that the action was performed by the user;
providing, via the user interface and based on the determining that the action was performed, at least one other interactive element of the one or more interactive elements, the at least one other interactive element including an additional request for the user to perform one or more additional actions;

determining, by the one or more processors, whether the one or more additional actions were satisfactorily performed by the user;

transmitting, based on the determining whether the one or more additional actions were satisfactorily performed, an electronic signal to an other electronic device, the electronic signal facilitating regulating access to a restricted location via a location-access point that is communicatively coupled, via electronic circuitry, with the electronic device; and wherein the action includes sanitizing a device contacting surface to be used, by the user, to touch the electronic device, and wherein the determining that the action was performed comprises detecting presence of the device contacting surface within a defined proximity of a liquid dispensing unit of the electronic device, and dispensing a liquid onto the device contacting surface.

9. The computer-implemented method of claim 8, wherein the method further comprises:

monitoring motion detection data via one or more sensors of a sensor unit of the electronic device, the motion detection data indicating whether at least one user has moved within a defined proximity to the sensor unit;

determining, based on the monitoring, that the user has entered the defined proximity to the sensor unit; and wherein the at least one interactive element is provided, via the user interface, based on the determining that the user has entered the defined proximity to the sensor unit.

10. The computer-implemented method of claim 8, wherein based on dispensing the liquid, the method further comprises:

tracking each instance of the liquid being dispensed and based thereon storing, in a remote database in communication with the one or more processors, a count corresponding to each instance of the liquid being dispensed;

determining that the count has reached a predetermined value; and based on the count reaching the predetermined value, distributing an electronic notification to a remotely connected electronic device, the electronic notification indicating that the liquid needs to be replenished.

11. The computer-implemented method of claim 8, wherein the additional request comprises a request that the user provide at least one of (i) identifying information of the user, (ii) a real-time temperature reading, or (iii) a response to each question of one or more questions presented via the user interface.

12. The computer-implemented method of claim 11, wherein the one or more questions presented via the user interface are remotely configurable.

13. The computer-implemented method of claim 11, wherein the determining, by the one or more processors, whether the one or more additional actions were satisfactorily performed by the user includes tracking each instance of the response, provided by the user, to each question of the one or more questions presented via the user interface and based on the tracking, storing, in a remote database in communication with the one or more processors, a count corresponding to each instance of the response provided by the user, wherein the method further comprises:

determining that the count has reached a predetermined value; and based on the count reaching the predetermined value, distributing an electronic notification to a remotely connected electronic device, the electronic notification indicating that the user interface needs to be cleaned.

14. The computer-implemented method of claim 8, wherein the additional request includes a request that the user provide a real-time temperature reading, and based thereon the determining that the one or more additional actions were performed by the user includes determining that the user has provided a real-time temperature reading within an acceptable temperature range.

15. The computer-implemented method of claim 8, wherein the determining, by the one or more processors, whether the one or more additional actions were performed by the user further includes receiving, by the one or more processors and via a temperature detection unit of the electronic device, a first temperature reading, and based thereon determining whether the first temperature reading is outside an acceptable temperature range, and wherein the method further comprises providing, via the user interface and based on the determining that the first temperature reading is outside the acceptable temperature range, an additional request of the one or more additional requests for the user to provide a second temperature reading, the second temperature reading to facilitate verifying whether the first temperature reading is accurate.

16. The computer-implemented method of claim 8, wherein the other electronic device includes an electronic relay, and wherein the determining whether the one or more additional actions were satisfactorily performed by the user includes determining that the one or more additional actions were satisfactorily performed by the user, and based thereon sending the electronic signal to the electronic relay, wherein the electronic relay facilitates providing access, based on receiving the electronic communication, to the restricted location to the user by completing a circuit of the location-access point.

17. A computer program product comprising:

a computer readable storage medium readable by a processing circuit and storing instructions for execution by the processing circuit for performing a method comprising:

providing, by one or more processors of the processing circuit and via a user interface of an electronic device, one or more interactive elements, the one or more interactive elements including a request for a user to perform an action;

determining, by the one or more processors, that the action was performed by the user;

providing, via the user interface and based on the determining that the action was performed, at least one other interactive element of the one or more interactive elements, the at least one other interactive element including an additional request for the user to perform one or more additional actions;

determining, by the one or more processors, whether the one or more additional actions were satisfactorily performed by the user;

transmitting, based on the determining whether the one or more additional actions were satisfactorily performed, an electronic signal to an other electronic device, the electronic signal facilitating regulating access to a restricted location via a location-access point that is communicatively coupled, via electronic circuitry, with the electronic device; and wherein the action includes sanitizing a device contacting surface to be used, by the user, to touch the electronic device, and wherein the determining that the action was performed comprises detecting presence of the device contacting surface within a defined proximity of a liquid dispensing unit of the electronic device, and dispensing a liquid onto the device contacting surface.

18. The computer program product of claim 17, wherein the method further comprises:

monitoring motion detection data via one or more sensors of a sensor unit of the electronic device, the motion detection data indicating whether at least one user has moved within a defined proximity to the sensor unit;

determining, based on the monitoring, that the user has entered the defined proximity to the sensor unit; and wherein the at least one interactive element is provided, via the user interface, based on the determining that the user has entered the defined proximity to the sensor unit.

19. The computer program product of claim 17, wherein the additional request comprises a request that the user provide at least one of (i) identifying information of the user, (ii) a real-time temperature reading, or (iii) a response to each question of one or more questions presented via the user interface.

20. The computer program product of claim 19, wherein the one or more questions presented via the user interface are remotely configurable.

21. The computer program product of claim 17, wherein the additional request includes a request that the user provide a real-time temperature reading, and based thereon the determining that the one or more additional actions were performed by the user includes determining that the user has provided a real-time temperature reading within an acceptable temperature range.

22. The computer program product of claim 17, wherein the determining, by the one or more processors, whether the one or more additional actions were performed by the user further includes receiving, by the one or more processors and via a temperature detection unit of the electronic device, a first temperature reading, and based thereon determining whether the first temperature reading is outside an acceptable temperature range, and wherein the method further comprises providing, via the user interface and based on the determining that the first temperature reading is outside the acceptable temperature range, an additional request of the one or more additional requests for the user to provide a second temperature reading, the second temperature reading to facilitate verifying whether the first temperature reading is accurate.

23. The computer program product of claim 22, wherein the acceptable temperature range is remotely configurable.

24. The computer program product of claim 17, wherein the other electronic device includes an electronic relay, and wherein the determining whether the one or more additional actions were satisfactorily performed by the user includes determining that the one or more additional actions were satisfactorily performed by the user, and based thereon sending the electronic communication to the electronic relay, wherein the electronic relay provides access, based on receiving the electronic communication, to the restricted location by completing a circuit of the location-access point, wherein the completed circuit facilitates granting access to the restricted location to the user.

25. A computer-implemented method comprising:

providing, by one or more processors and via a user interface of an electronic device, one or more interactive elements, the one or more interactive elements including a request for a user to perform an action;

determining, by the one or more processors, that the action was performed by the user;

providing, via the user interface and based on the determining that the action was performed, at least one other interactive element of the one or more interactive elements, the at least one other interactive element including an additional request for the user to perform one or more additional actions;

determining, by the one or more processors, that the one or more additional actions were not satisfactorily performed by the user;

based on the determining that the one or more additional actions were not satisfactorily performed by the user, sending, by the one or more processors, a notification to an other electronic device of an other user; and wherein the action includes sanitizing a device contacting surface to be used, by the user, to touch the electronic device, and wherein the determining that the action was performed comprises detecting presence of the device contacting surface within a defined proximity of a liquid dispensing unit of the electronic device, and dispensing a liquid onto the device contacting surface.

26. The computer-implemented method of claim 25, wherein the notification indicates that the user did not satisfactorily perform the one or more additional actions.

27. The computer-implemented method of claim 25, wherein the additional request comprises a request that the user provide a response to each question of one or more questions presented via the user interface.

28. The computer-implemented method of claim 27, based on the determining that the one or more additional actions were not satisfactorily performed, the method further comprises receiving, from the other electronic device of the other user, in real time one or more personalized questions from the other user, and based thereon displaying the one or more personalized questions via the user interface.

* * * * *